United States Patent [19]
Yokura et al.

[11] Patent Number: 5,849,801
[45] Date of Patent: Dec. 15, 1998

[54] 4-AMINO-5-OXY-2,6,6-TRIMETHYL-2-CYCLOHEPTENE COMPOUNDS

[75] Inventors: Susumu Yokura; Masao Yajima; Kiyokazu Murakami; Kouichi Matsunaga, all of Tokyo, Japan

[73] Assignee: Tokyo Tanabe Company Limited, Tokyo, Japan

[21] Appl. No.: 903,076

[22] PCT Filed: Apr. 12, 1996

[86] PCT No.: PCT/JP96/01023

§ 371 Date: Jul. 30, 1997

§ 102(e) Date: Jul. 30, 1997

[87] PCT Pub. No.: WO96/32370

PCT Pub. Date: Oct. 17, 1996

[30] Foreign Application Priority Data

Apr. 12, 1995 [JP] Japan ..................... 7-087294

[51] Int. Cl.⁶ .................................................. A61K 31/135
[52] U.S. Cl. ..................... 514/683; 514/506; 514/646; 514/579; 514/428; 514/317; 514/212; 514/238.8; 514/255; 514/327; 514/330; 514/278; 514/331; 540/610; 544/173; 544/399; 548/571
[58] Field of Search ................. 564/1, 355, 431, 564/219, 218; 560/45; 548/571; 546/237, 221, 227, 207, 223; 540/60; 544/173, 399; 514/653, 506, 646, 579, 428, 317, 212, 238.8, 255, 327, 330, 278, 331

[56] References Cited

FOREIGN PATENT DOCUMENTS

| | | |
|---|---|---|
| 3-275640 | 12/1991 | Japan . |
| 5-213811 | 8/1993 | Japan . |
| 7-17852 | 1/1995 | Japan . |
| 7-101858 | 4/1995 | Japan . |

OTHER PUBLICATIONS

Chini et al., 1990, Metal Salts as New Catalysts . . . Tetrahedron Letters.
Corey et al., 1986, A New Synthetic Route To Prostaglandins, Tetrahedron Letters.
Iwamoto et al., Dec. 1986, Prophylactic Effect Of . . . Japanese Pharmacology & Therapeutics.
Minami et al., 1983, Japanese Journal of Thoracic Diseases.
Ishibashi et al., 1983, Folia Pharmacologica Japonica.
Suzuki et al., Sep. 1987, The Clinical Report vol. 21 No. 13.

Primary Examiner—Brian M. Burn
Attorney, Agent, or Firm—McGlew and Tuttle

[57] ABSTRACT

4-amino-5-oxy-2,6,6-tri methyl-2-cycloheptene compounds represented by the following general formula:

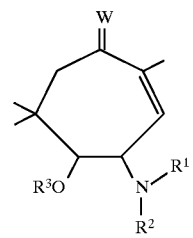

(wherein $R^1$ and $R^2$ each independently represent a hydrogen atom, an alkyl group which may have a substituent, or a phenyl group which may have a hydroxyl group, lower alkoxy group, amino group, nitro group, carboxyl group, lower alkoxycarbonyl group or halogen atom, or $R^1$, $R^2$ and the nitrogen atom together represent a saturated nitrogen heterocyclic group; $R^3$ represents a hydrogen atom, a lower alkyl group or a lower aliphatic acyl group); and W represents an oxo group, oxime group or oxime ether group; and their pharmacologically acceptable salts and solvates.

The 4-amino-5-oxy-2,6,6-trimethyl-2-cycloheptene compounds exhibit an effect against rat peripheral arterial occlusion models, spontaneous hypertensive rats and histamine-induced airway contraction models, and are thus useful as remedy for hypertension, peripheral arterial occlusion and bronchial asthma.

7 Claims, 1 Drawing Sheet

4-AMINO-5-OXY-2,6,6-TRIMETHYL-2-CYCLOHEPTENE COMPOUNDS

THE DESCRIPTION

This application is a 35 U.S.C. 371 of PCT/JP96/01023 (Apr. 12, 1996).

TECHNICAL FIELD

The present invention relates to 4-amino-5-oxy-2,6,6-trimethyl-2-cycloheptene compounds which are useful as medicaments, and to their pharmacologically acceptable salts and solvates. More specifically, it relates to a remedy for hypertension, peripheral arterial occlusion or bronchial asthma whose effective components are 4-amino-5-oxy-2, 6,6-trimethyl-2-cycloheptene compounds, their pharmacologically acceptable salts and their solvates.

BACKGROUND ART

The present inventors have isolated and identified 4,5-dihydroxy-2,6,6-trimethyl-2-cyclohepten-1-one (hereunder referred to as "Saishin N") from the crude drug Asarum Siebeldi, as a useful antiulcer substance, and have developed a method for its chemical production, filing a patent application therefor (Japanese Unexamined Patent Publication No. Hei-3-275640) as well as a patent application for various Saishin N compounds with antiulcer effects (Japanese Unexamined Patent Publication No. Hei-5-213811).

It was found that the Saishin N compounds are effective for the treatment of ischemic and reperfusion disorders and the improvement of microcirculatory blood flow, and patent applications were filed therefor (Japanese Unexamined Patent Publication Nos. Hei-7-17852, Hei-7-101858).

DISCLOSURE OF THE INVENTION

The present Inventors have diligently researched aminolysis reactions of eucarvone-4,5-oxide for the purpose of synthesizing Saishin N compounds with amino groups, and have completed the present invention based upon the finding that Saishin N compounds with an amino group selectively introduced at position 4 may be obtained by using the method of Marco Chini et al. [Tetrahedron Letters, Vol. 31, 4661 (1990)], and that the resulting 4-amino-5-oxy-2,6,6-trimethyl-2-cyclohepten-1-one compounds and their oxime derivatives exhibit an effect against rat peripheral arterial occlusion models, spontaneous hypertensive rats, histamine-induced airway contraction models and passive sensitization models.

According to the present invention there are provided 4-amino-5-oxy-2,6,6-trimethyl-2-cycloheptene compounds represented by the following general formula:

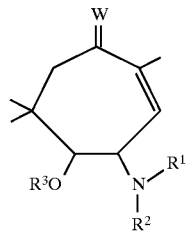

(wherein $R^1$ and $R^2$ each independently represent a hydrogen atom, an alkyl group, or a phenyl group which may have a hydroxyl group, lower alkoxy group, amino group, nitro group, carboxyl group, lower alkoxycarbonyl group or halogen atom, or $R^1$, $R^2$ and the nitrogen atom together represent a saturated nitrogen heterocyclic group; $R^3$ represents a hydrogen atom, a lower alkyl group or a lower aliphatic acyl group; and W represents an oxo group, oxime group or oxime ether group); and their pharmacologically acceptable salts and their solvates, as well as pharmaceutical composition containing then as an effective ingredient.

The alkyl group is an acyclic or cyclic alkyl group of 1 to 10 carbon atoms, and preferably 1 to 8 carbon atoms, and it may be substituted with a hydroxyl group, lower alkoxy group, amino group, lower alkylamino group, lower dialkylamino group, or a phenyl group which may have a hydroxyl group, lower alkoxy group, amino group, nitro group, carboxyl group, lower alkoxycarbonyl group or halogen atom. Specific examples thereof include methyl, ethyl, propyl, isopropyl, butyl, isobutyl, sec-butyl, tert-butyl, isopentyl, neopentyl, tert-pentyl, hexyl, isohexyl, heptyl, octyl, cyclopropyl, cyclobutyl, cyclopentyl, cyclohexyl, cycloheptyl, cyclooctyl, 2-hydroxyethyl, 2-methoxyethyl, 2-dimethylaminoethyl, benzyl, 4-ethoxycarbonylbenzyl, phenethyl and 4-phenylbutyl groups.

The halogen atom may be fluorine, chlorine, bromine or iodine.

The saturated nitrogen heterocyclic group is pyrrolidine, piperidine, homopiperidine, piperazine, homopiperazine or morpholine which may have a lower alkyl group, hydroxyl group, lower alkoxy group, carboxyl group, lower alkoxycarbonyl group, oxo group or an acetal group thereof on its ring.

The oxime ether is a lower alkyloxime ether or benzyloxime ether.

The term "lower" here refers to an acyclic or cyclic saturated hydrocarbon group of 1 to 4 carbon atoms.

Pharmacologically acceptable salts of the compounds of the invention include salts of inorganic acids such as hydrochloric acid, hydrobronic acid, hydroiodic acid, sulfuric acid and phosphoric acid; salts of organic acids such as acetic acid, tartaric acid, fumaric acid and maleic acid; salts of sulfonic acids such as methanesulfonic acid, ethanesulfonic acid, camphorsulfonic acid, benzenesulfonic acid and toluenesulfonic acid; and salts of alkali metals or alkaline earth metals such as sodium, potassium and calcium.

In addition, solvates (including hydrates) of the compounds of the invention which may be produced by common methods from free compounds of the invention and their salts are also encompassed within the present invention.

Stereoisomers of the compounds of the invention exist which are derived from the asymmetrical carbon atoms at positions 4 and 5 of the cycloheptene ring and from oximes, and all of these stereoisomers and their mixtures are also included within the present invention.

A method of producing the compounds of the invention will now be explained.

4-amino-5-oxy-2,6,6-trimethyl-2-cyclohepten-1-one (compound A) may be obtained by subjecting eucarvone-4, 5-oxide to an aminolysis reaction in the presence of a metal salt.

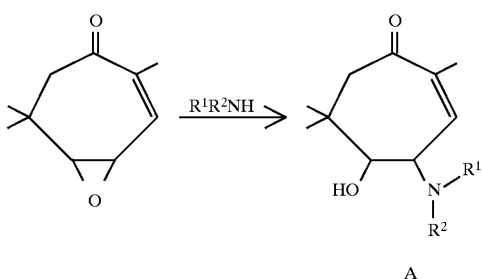

A (where $R^1$ and $R^2$ are the same as defined above.)

The metal salt used for the reaction may be a perchlorate such as lithium perchlorate, magnesium perchlorate or sodium perchlorate; a chloride such as calcium chloride or zinc chloride; or a trifluoromethanesulfonate of a lanthanide, such as ytterbium trifluoromethanesulfonate, neodymium. trifluoromethanesulfonate or gadolinium trifluoromethanesulfonate.

The reaction solvent may be any one which does not inhibit the reaction, and acetonitrile may be used when the metal salt is a perchlorate or chloride, while methylene chloride or benzene may be used when the metal salt is a lanthanide trifluoromethanesulfonate.

Compound B wherein $R^2$ of compound A is a hydrogen atom may be N-alkylated to obtain compound C.

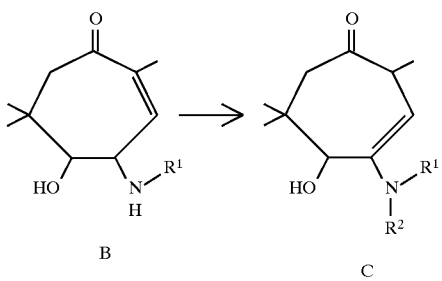

(where $R^1$ is as defined above, and $R^2$ represents a lower alkyl group.)

The N-alkylation may be accomplished by a method of treatment with an aldehyde under reductive conditions, or a method of treatment with an alkylating agent such as a lower alkyl halide.

Methylation with an aldehyde may be accomplished by heating in formic acid. An alcohol such as methanol or ethanol may be added as a reaction solvent.

Compound A may be oximated to obtain compound D.

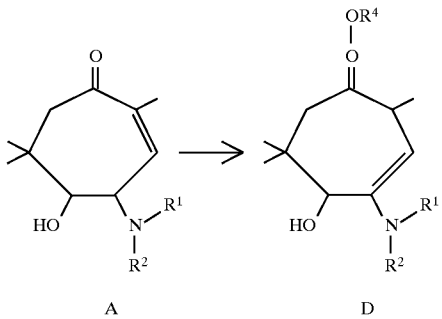

(wherein $R^1$ and $R^2$ each independently represent a hydrogen atom, an alkyl group which may have a substituent, or a phenyl group which may have a hydroxyl group, lower alkoxy group, amino group, nitro group, carboxyl group, lower alkoxycarbonyl group or halogen atom, or $R^1$, $R^2$ and the nitrogen atom together represent a saturated nitrogen heterocyclic group; and $R^4$ represents a hydrogen atom, lower alkyl group or benzyl group.)

The oximation may be accomplished according to the method of E. J. Corey [Tetrahedron Letters, Vol. 27, 2199 (1986)], whereby compound A is reacted with the hydrochloride of a hydroxylamine or alkoxylamine in methanol in the presence of pyridine.

Protection of the amino group or hydroxyl group of compound B with an acyl group and the oxo group with a methyloxime ether may be followed by alkylation of the hydroxyl group with a lower alkyl halide and then removal of the protecting groups to obtain compound E.

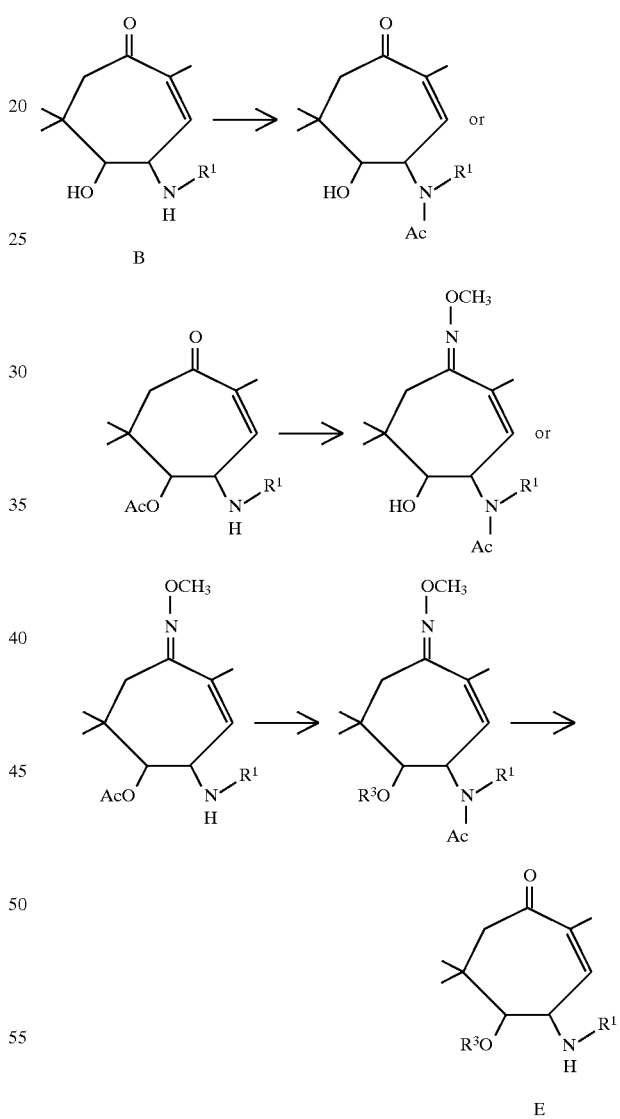

(wherein $R^1$ represents a hydrogen atom, an alkyl group which may have a substituent, or a phenyl group which may have a hydroxyl group, lower alkoxy group, amino group, nitro group, carboxyl group, lower alkoxycarbonyl group or halogen atom, and $R^3$ represents a lower alkyl group.)

The acyl group may be a carboxylic acyl group such as acetyl, trifluoroacetyl or benzoyl, or a carbamate acyl group such as tert-butyloxycarbonyl or benzyloxycarbonyl.

In the above-mentioned acetylation reaction, acetylation of the amino group occurs when $R^1$ is an alkyl group which may have a substituent, and acetylation of the hydroxyl group occurs when $R^1$ is a phenyl group. However, the acetyl group on the hydroxyl group is transferred to the amino group during the alkylation reaction, to obtain the O-alkylated compound E.

The alkylation may be accomplished by using a lower alkyl halide in the presence of a suitable base.

The base may be a metal alkoxide such as sodium methoxide, sodium ethoxide or potassium tert-butoxide, or sodium hydride, potassium hydride, sodium amide, butyl lithium or lithium diisopropylamide.

The solvent used for the reaction may be an ether such as diethyl ether, dimethoxyethane, tetrahydrofuran or dioxane, or a polar aprotic solvent such as dimethylformamide or dimethylsulfoxide.

The protecting groups may be removed by heating in appropriately diluted hydrochloric acid, hydrobromic acid or sulfuric acid.

Effect

The pharmacological effects of the compounds of the invention will now be explained in detail.

[Effect on rat peripheral arterial occlusion models]

Models were prepared following the method of Iwamoto et al. (Iwamoto, M. et al., Japanese Pharmacology & Therapeutics, Vol. 14, Suppl. 5, p. 41, 1986). Upon minimal dissection of the femoral regions of SD rats (6 per group) with a body weight of 250~350 g under Nembutal anesthesia, 0.1 ml of 5% lactic acid was administered intraarterially. The rats were raised for 14 days under normal conditions, and observed for lesions of the lower legs. The grading for the lesions was: "1" for nigrities only at the nail tips, "2" for nigrities up to the digits, "3" for necrosis of the digits, and "4" deciduation of the digits. Each of the digits of the lower legs on the side where lactic acid had been administered were graded, and the overall grade was determined as the index of lesions. The disorder inhibition rate was determined by dividing the index of lesions in the drug-administered group by the index of lesions of the control group. The drugs were dissolved in physiological saline or dimethylsulfoxide, and injected through the caudal vein 5 minutes prior to injection of the 5% lactic acid. As shown in Table 1, the compounds of the invention inhibited occurrence of peripheral arterial occlusion.

TABLE 1

Effect on rat peripheral arterial occlusion models

| Compound | Solvent | Dosage (mg/kg, i.v.) | Inhibition rate (%) |
|---|---|---|---|
| Compound of Example 1 | physiological saline | 5 | 42* |
| Compound of Example 16 | | 3 | 65* |
| | | 30 | 78** |
| Compound of Example 5 | DMSO | 5 | 35* |

*p<0.05
**p<0.02

[Effect on guinea pig bronchoconstriction]

After urethane anesthetization of male Hartley guinea pigs (body weight: 350~450 g, 5 per group, Nihon Crea Co.), a small cannula was inserted into trachea. Next, gallamine triethiodide (1 mg/kg) was intravenously administered, and the tracheal cannula was connected to a constant volume respirator. The artificial respiration was conducted with an air volume per breath of 7~10 ml, a breath frequency of 60/min and a lung application pressure of 10 cm water. The volume of air overflowing from the legs on the cannula side was recorded on a polygraph (RM6100: product of Nihon Koden Co.) with a model 7020 bronchospasm transducer (product of Ugo Basile). Hydrochloride of the test compounds were dissolved in physiological saline, and inhalation was performed with reference to the method of Minami et al. (Minami, S. et al., Japanese Journal of Thoracic Diseases, Vol. 21, No. 3, p. 252, 1983). The inhalation load apparatus was prepared by directly incorporating an ultrasonic nebulizer into an artificial respiration circuit (Omron ultrasonic aspirator NE-U11B, product of Tateishi Electric Co.). The test compound (mg/0.5 ml) was administered by inhalation for 30 seconds, and after 2 minutes histamine (3 µg/kg) was intravenously administered and the air overflow volume was measured. The bronchoconstriction rate was calculated as a percentage with 100 being the height of contraction when the airway was completely constricted. The inhibition rate was calculated by dividing the contraction rate of the test compound group by the contraction rate of the control group. As shown in Table 2, the compounds of the invention inhibited bronchoconstriction.

TABLE 2

Effect on histamine-induced guinea pig bronchoconstriction models

| Compound | Dosage (mg/0.5 ml) | Brochoconstriction inhibition rate (%) |
|---|---|---|
| Compound of Example 9 | 1.0 | 57*** |
| Compound of Example 15 | 3.0 | 73*** |
| Compound of Example 16 | 3.0 | 32** |
| Compound of Example 16 | 10.0 | 46*** |
| Compound of Example 22 | 3.0 | 17* |
| Compound of Example 23 | 3.0 | 23* |
| Compound of Example 26 | 3.0 | 53** |
| Compound of Example 30 | 3.0 | 42** |
| (-) Compound of Example 35 | 10.0 | 64*** |

*p<0.05
**p<0.02
***p<0.01

[Effect on antigen-induced guinea pig bronchoconstriction]

Male Hartley guinea pigs (body weight: 300~450 g, Nihon Crea Co.) were intraperitonealy administered anti-DNP-Ascarls serum (1024-fold antibody titer) at 0.5 ml/kg. After 24 hours, under urethane anesthesia there were inserted a cannula into the trachea, a sphygmomanometric cannula into the left cervical artery and a drug injection cannula into the right jugular vein, and gallamine triethiodide (1.0 mg/0.5 ml/kg) was intravenously administered and connected to an artificial respirator (product of Ugo Basile). For the test, diphenhydramine (60 mg/ml/kg) was intraperitoneally administered, the compound of Example 16 was inhaled as the test compound after 14 minutes, and following intravenous administration of DNP-bovine serum albumin (1.0 mg protein/0.5 ml/kg) one minute after administration of the test compound, the degree of bronchoconstriction was observed over a period of 15 minutes. The bronchoconstriction rate was given as a percentage of the maximum air over flow volume obtained by clamping off the trachea. The test compounds were inhaled by nebulizing for 30 seconds with an ultrasonic nebulizer. As shown in FIG. 1, the compounds of the invention inhibited airway contract ion.

[Effect on blood pressure of anesthetized rats]

Male SD rats (body weight: 250~350 g, product of Nihon Crea Co.) were placed under urethane anesthesia and then a sphygmomanometric pressure transducer was inserted into the left cervical artery and recording was made on a polygraph (RM6100, product of Nihon Koden Co.) using a strain pressure amp (AP-621G, product of Nihon Koden Co.). The test compounds were dissolved in physiological saline and administered intravenously. The change in blood pressure was indicated as the reduction rate from the initial value of diastolic blood pressure just prior to administration of the test compound. As shown in Table 3, the compounds of the invention lowered the blood pressure of anesthetized rats.

TABLE 3

Effect on blood pressure of anesthetized rats

| Compound | Reduction of blood pressure (%) Dosage (mg/kg) | | |
|---|---|---|---|
| | 1 | 3 | 10 |
| Compound of Example 2 | 16 | 31 | |
| Compound of Example 7 | | | 34 |
| Compound of Example 8 | | | 45 |
| Compound of Example 9 | 14 | 32 | 51 |
| Compound of Example 12 | | | 33 |
| Compound of Example 13 | | | 28 |
| Compound of Example 15 | | | 26 |
| Compound of Example 16 | 6 | 16 | 40 |
| Compound of Example 17 | | | 42 |

[Effect on spontaneous hypertensive rats (SHR)]

Male SHRs (body weight: 270~300 g, Nihon Charles River Co.) which had been raised for at least one week were subjected to blood pressure measurement twice, on the day of the test and the day prior thereto, and the average values were used as initial values. The systolic blood pressure was measured by the tail-cuff method, using a noninvasive sphygmomanometer (Programmed Electro-Sphygmomanometer PE-300: Narco Bio-Systems, Inc.). The test compounds were dissolved or suspended in a 0.5% methyl cellulose solution and administered orally, and at 3 hours after administration the blood pressure was measured. During the blood pressure measurement, the animals were warmed for 15 minutes in an incubator. As shown in Table 4, the compounds of the invention reduced SHR blood pressure.

TABLE 4

Effect on SHR blood pressure

| Compound | Dosage (mg/kg, i.v.) | Reduction of blood pressure (%) |
|---|---|---|
| Compound of Example 7 | | 17 |
| Compound of Example 8 | | 11 |
| Compound of Example 9 | | 8 |
| Compound of Example 10 | 10 | 13 |
| Compound of Example 13 | | 7 |
| Compound of Example 15 | | 8 |
| Compound of Example 16 | | 15 |
| Compound of Example 17 | | 9 |
| Enalapril | 5 | 18 |

[Inhibiting effect on platelet aggregation (in vitro)]

Platelet rich plasma was prepared from Japanese white male house rabbits (body weight: 2.5~3.0 kg) following the method of Suzuki et al. (Suzuki, K. et al., The Clinical Report, Vol. 21, No. 13, p. 5263, 1987). The resulting platelet rich plasma solution was appropriately diluted with a Tris-Tyrode buffer solution (pH 7.4) to prepare a $4 \times 10^5$ platelet/$\mu$l platelet suspension to be used for the test. The platelet aggregation was measured using a platelet aggregometer (NBS Hematoracer 601, product of Nikoh Bioscience Co.). Specifically, 250 $\mu$l of the platelet suspension, 5 $\mu$l of a 96 mM calcium chloride solution and 5 $\mu$l of the test compound solution dissolved in methanol were added to a cuvette, and after incubating for one minute at 37° C., 20 $\mu$l of an aggregating agent was added and the maximum degree of aggregation occurring was determined. The aggregating agents used were platelet activating factor (PAF) (2.5 ng/ml) and arachidonic acid (68.6 $\mu$g/ml). The 50% inhibition concentration ($IC_{50}$) was calculated from the results of measurement with various concentrations of each test compound. As shown in Table 5, the compounds of the invention inhibited platelet aggregation.

TABLE 5

Inhibiting effect on platelet aggregation

| Compound | $IC_{50}$ ($\mu$M) | |
|---|---|---|
| | RAF | Arachidonic acid |
| Compound of Example 1 | | 100 |
| Compound of Example 3 | 26 | 36 |
| Compound of Example 4 | 37 | 69 |
| Compound of Example 5 | 66 | 100 |
| Compound of Example 16 | | 100 |
| Compound of Example 18 | 98 | |
| Compound of Example 28 | | 11 |

[Effect on calcium contraction (in vitro)]

This was investigated according to the method of Ishibashi, et al. (Ishibashi, A. et al., Folia Pharmacologica Japonica, Vol. 82, p. 361, 1983). Male SD rats of body weight approximately 300 g were used to prepare thoracic aorta extract specimens, which were suspended and immobilized in a organ bath containing 10 ml of Krebs-Henseleit buffer solution at 37° C. through which a mixed gas of oxygen (95%) and carbon dioxide (5%) had been passed. After equilibrating the specimens, they were equilibrated in a buffer solution without calcium chloride and then in an isotonic calcium-free 80 mM potassium chloride buffer solution replaced with potassium ions, and a resting tension of 0.2 g was applied. Contraction was induced by addition of 0.3 mM calcium chloride. The test compounds were added 10 minutes prior to addition of the calcium solution. The percent inhibition of the test compounds were calculated using the first contraction as the control (100% contraction). The test compounds were used for the test as solutions in dimethylsulfoxide at a $1 \times 10^{-7}$M concentration. As shown in Table 6, the compounds of the invention inhibited calcium contraction of the thoracic aorta.

TABLE 6

Effect on calcium chloride contraction

| Compound | Contraction Inhibition (%) |
|---|---|
| Compound of Example 1 | 48 |
| Compound of Example 4 | 33 |
| Compound of Example 10 | 32 |
| Compound of Example 16 | 24 |
| Compound of Example 18 | 39 |
| Compound of Example 22 | 48 |

These results show that the compounds of the invention are useful as a remedy for arterial occlusion, hypertension, peripheral arterial occlusion and bronchial asthma.

The compounds of the invention may be combined with common pharmaceutical carriers to prepare solid preparations such as tablets, hard or soft capsules, granules, powder, fine granules or suppositories, or liquid preparations such as injections, inhalants, syrups, aqueous mixtures, suspensions or emulsions. The combined pharmaceutical carrier may be appropriately selected depending on the desired form of preparation, examples thereof being excipients, binders, disintegrators, lubricants, coating agents, solution adjuvants, emulsifiers, suspending agents, surfactants, inhalation aids, stabilizers and solvents. The amount thereof to be used will differ depending on the age, symptoms and mode of administration, but oral administration is generally 0.1~1000 mg/day, either once or in divided doses.

BEST MODE FOR CARRYING OUT THE INVENTION

Figure 1:
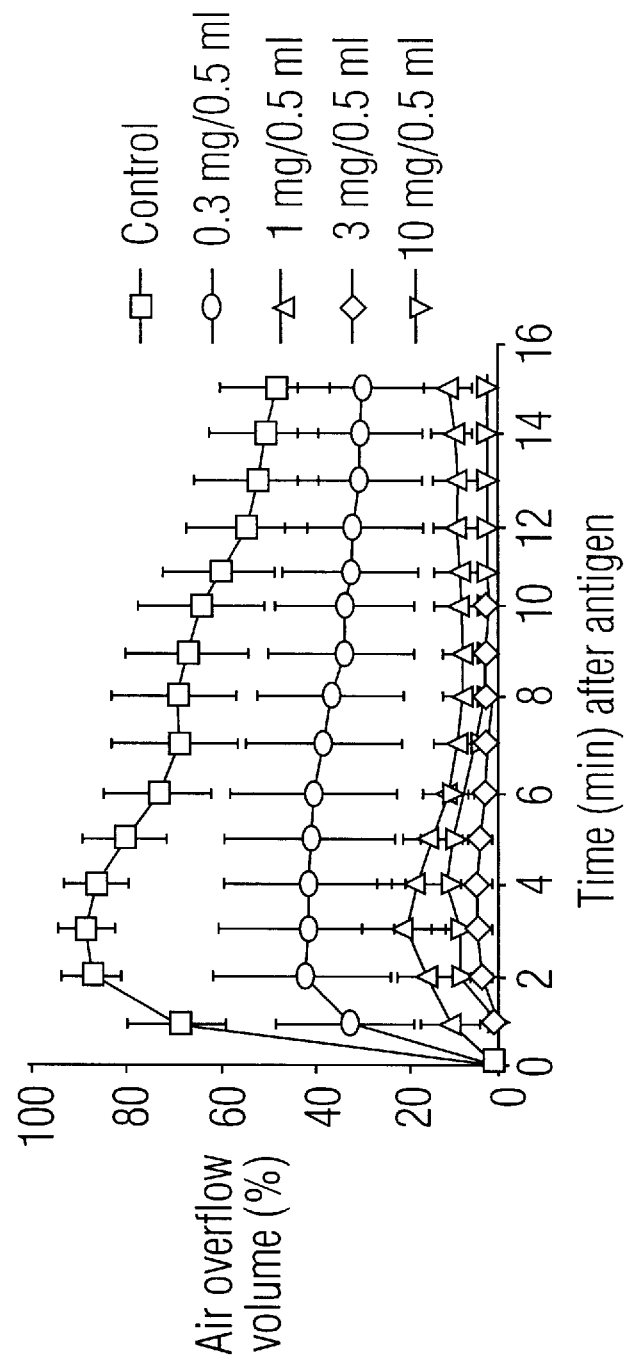
FIG. 1 is a graph showing the effect on antigen-induced guinea pig airway contraction.

The following examples serve to explain the present invention, but are in no way intended to restrict it.

EXAMPLE 1

4-benzylamino-5-hydroxy-2,6,6-trimethyl-2-cyclohepten-1-one

Lithium perchlorate (5.3 g, 50 millimoles) and benzylamine (5.4 ml, 50 millimoles) were added to an acetonitrile solution (50 ml) containing eucarvone-4,5-oxide (8.5 g, 50 millimoles), and the mixture was heated to reflux for 10 hours. The reaction solution was concentrated, water was added and the resulting aqueous solution was subjected to extraction with ethyl acetate. After washing the ethyl acetate solution with brine, it was dried over anhydrous magnesium sulfate. The residue obtained from concentrating the ethyl acetate solution was purified by silica gel column chromatography using benzene/ethyl acetate (5:1) as the eluent, to obtain 7.52 g (55%) of 4-benzylamino-5-hydroxy-2,6,6-trimethyl-2-cyclohepten-1-one as a yellow oil.

$^1$H-NMR(CDCl$_3$,ppm):0.88(3H,s),1.12(3H,s),1.84(3H,t,J=2 Hz),2.30(1H,d,J=12 Hz),2.45(1H,d,J=12 Hz),3.07(1H,d,J=9 Hz),3.30(dm,J=9 Hz),3.85(1H,d,J=13 Hz),4.06(1H,d,J=13 Hz),6.44(1H,br),7.27~7.36(5H,m)

The resulting free base (5.47 g, 20 millimoles) was dissolved in ethyl acetate (30 ml), and a 4N HCl-ethyl acetate solution (6 ml) was added. The precipitating crystals were filtered to obtain 6.07 g (98%) of hydrochloride as colorless needles. The melting point was 203°~204° C. (decomposition). The compounds of Examples 2 through 27 were obtained in the same manner as in Example 1.

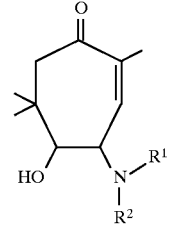

| Example | R$^1$ | R$^2$ |
|---|---|---|
| 1 | H | —CH$_2$—Ph |
| 2 | H | —(CH$_2$)$_2$—Ph |
| 3 | H | —C$_6$H$_4$—CO$_2$Et.p |
| 4 | H | —CH$_2$—C$_6$H$_4$—CO$_2$Et.p |
| 5 | H | —Ph |

-continued

| Example | R$^1$ | R$^2$ |
|---|---|---|
| 6 | H | —(CH$_2$)$_4$.Ph |
| 7 | H | cyclopentyl |
| 8 | H | cyclohezyl |
| 9 | H | —(CH$_2$)$_3$CH$_3$ |
| 10 | H | —(CH$_2$)$_2$—OCH$_3$ |
| 11 | H | —(CH$_2$)$_7$CH$_3$ |
| 12 | H | —C(CH$_3$)$_3$ |
| 13 | —CH$_2$CH$_3$ | —CH$_2$CH$_3$ |
| 14 | —(CH$_2$)$_2$CH$_3$ | —(CH$_2$)$_2$CH$_3$ |
| 15 | —(CH$_2$)$_4$— | |
| 16 | —(CH$_2$)$_5$— | |
| 17 | —(CH$_2$)$_6$— | |
| 18 | —(CH$_2$)$_2$—O—(CH$_2$)$_2$— | |
| 19 | —CH=(CH$_2$)$_4$— (with CH$_3$) | |
| 20 | —CH$_2$—CH(CH$_3$)—(CH$_2$)$_3$— | |
| 21 | —(CH$_2$)$_2$—CH(CH$_3$)—(CH$_2$)$_2$— | |
| 22 | —(CH$_2$)$_2$—N(CH$_3$)—(CH$_2$)$_2$— | |
| 23 | —(CH$_2$)$_2$—CH(OH)—(CH$_2$)$_2$— | |
| 24 | —(CH$_2$)$_2$—CH(CO$_2$Et)—(CH$_2$)$_2$— | |
| 25 | —(CH$_2$)$_2$—CH(CO$_2$H)—(CH$_2$)$_2$— | |
| 26 | —(CH$_2$)$_2$—(dioxolane)—(CH$_2$)$_2$— | |
| 27 | —(CH$_2$)$_2$—C(=O)—(CH$_2$)$_2$— | |

EXAMPLE 2

4-(2-phenylethylamino)-5-hydroxy-2,6,6-trimethyl-2-cyclohepten-1-one

32% yield, colorless prisms, melting point: 100.5°~101.5° C.

$^1$H-NMR(CDCl$_3$,ppm):0.97(3H,s),1.13(3H,s), 1.80(3H,t,J=2 Hz),2.32(1H,d,J=12 Hz),2.48(1H,d,J=12 Hz),2.81~2.96 (3H,m),3.01(1H,d,J=9 Hz),3.11~3.22(2H,m),4.85(1H,br), 6.25(1H,m),7.22~7.30(5H,m)

Hydrochloride: 89% yield, colorless crystals, melting point: 188.5°~190.5° C. (decomposition)

EXAMPLE 3

4-(4-ethoxycarbonylphenylamino)-5-hydroxy-2,6,6-trimethyl-2-cyclohepten-1-one

28% yield, colorless needles, melting point: 123°~124.5° C.

$^1$H-NMR (CDCl$_3$+D$_2$O,ppm): 1.08(3H,s),1.17(3H,s),1.37 (3H,t,J=7 Hz),1.83(3H,t,J=2 Hz),2.45(1H,d,J=12 Hz),2.67 (1H,d,J=12 Hz),3.41(1H,d,J=9 Hz),4.19(1H,dm),4.33(2H,q, J=7 Hz),6.35(1H,m),6.68(2H,d,J=9 Hz),7.92(2H,d,J=9 Hz)

EXAMPLE 4

5-hydroxy-4-(4-ethoxycarbonylbenzylamino)-2,6,6-trimethyl-2-cyclohepten-1-one

43% yield, light yellow oil $^1$H-NMR(CDCl$_3$,ppm): 0.90(3H,s),1.14(3H,s),1.40(3H,t, J=7 Hz),1.86(3H,t,J=2 Hz),2.32(1H,d,J=12 Hz),2.45(1H,d, J=12 Hz),3.13(1H,d,J=9 Hz),3.29(1H,m),3.94(1H,d,J=14 Hz),4.14(1H,d,J=14 Hz),4.38(2H,d,J=7 Hz),6.44(1H,m), 7.44(2H,d,J=8 Hz),8.04(2H,d,J=8 Hz)

EXAMPLE 5

5-hydroxy-4-phenylamino-2,6,6-trimethyl-2-cyclohepten-1-one

62% yield, light yellow oil

Hydrochloride: 94% yield, colorless crystals, melting point: 173°~178° C. (foaming decomposition)

$^1$H-NMR(CDCl$_3$,ppm): 0.97(3H,s),1.04(3H,s),1.79(3H,t, J=2 Hz),2.41(1H,d,J=12 Hz),2.44(1H,d,J=12 Hz),3.77(1H, d,J=9 Hz),4.33(1H,dm),6.44(1H,m),7.51(3H,m),7.81(2H, m)

EXAMPLE 6

4-(4-phenyl-1-butylamino)-5-hydroxy-2,6,6-trimethyl-2-cyclohepten-1-one

41% yield, colorless oil $^1$H-NMR(CDCl$_3$,ppm):0.96(3H,s),1.12(3H,s),1.58(2H, m),1.69(2H,m),1.81(3H,t,J=2 Hz),2.31(1H,d,J=12 Hz),2.48 (1H,d,J=12 Hz),2.63(3H,m),2.89(1H,m),3.00(1H,d,J=9 Hz), 3.0~3.5(1H,br,overlapping),3.18(1H,m),6.33(1H,brs), 7.1~7.3(5H,m)

Hydrochloride: 89% yield, colorless crystals

EXAMPLE 7

4-cyclopentylamino-5-hydroxy-2,6,6-trimethyl-2-cyclohepten-1-one hydrochloride

27% yield, colorless needles, melting point: 164°~166° C.

$^1$H-NMR(CDCl$_3$,ppm): 1.06(3H,s),1.13(3H,s),1.6~1.8 (2H,m),1.89(3H,t,J=2 Hz),1.9~2.2(6H,m),1.94(2H,s),3.65 (1H,br),3.76(1H,br),3.92(1H,br),5.32(1H,br),6.93(1H,m), 8.56(1H,br),9.99(1H,br)

EXAMPLE 8

4-cyclohexylamino-5-hydroxy-2,6,6-trimethy-2-cyclohepten-1-one hydrochloride

31% yield, colorless needles, melting point: 195°~197° C. (decomposition)

$^1$H-NMR(CDCl$_3$,ppm): 1.05(3H,s),1.13(3H,s),1.30(3H, m),1.70(5H,m),1.89(3H,t,J=2 Hz),2.23(2H,m),2.47(2H,s), 3.24(1H,br),3.67(1H,d,J=9 Hz),5.36(1H,br),6.89(1H,m), 8.37(1H,br),9.88(1H,br)

EXAMPLE 9

4-(1-butylamino)-5-hydroxy-2,6,6-trimethyl-2-cyclohepten-1-one hydrochloride

22% yield, colorless crystals, melting point: 151°–154° C.

$^1$H-NMR(CDCl$_3$,ppm): 0.98(3H,t,J=7 Hz),1.08(3H,s), 1.15(3H,s),1.48(2H,m),1.91(5H,m),2.42(1H,d,J=12 Hz), 2.49(1H,d,J=12 Hz),3.05(1H,m),3.19(1H,m),3.51(1H,m), 4.14(1H,br),4.64(1H,brd),6.67(1H,m),9.23(1H,br),9.45(1H, br)

EXAMPLE 10

5-hydroxy-4-(2-methoxyethylamino)-2,6,6-trimethyl-2-cyclohepten-1-one

24% yield, light brown crystals $^1$H-NMR(CDCl$_3$,ppm): 0.98(3H,s),1.15(3H,s),1.83(3H,t, J=2 Hz),2.33(1H,d,J=12 Hz),2.50(1H,d,J=12 Hz),2.82(1H, m),3.06(2H,m),3.23(1H,m),3.39(3H,s),3.53(2 H,m),6.40 (1H,m)

Hydrochloride: 92% yield, light brown crystals

EXAMPLE 11

4-(1-octylamino)-5-hydroxy-2,6,6-trimethyl-2-cyclohepten-1-one hydrochloride

15% yield, colorless crystals, melting point: 114°~118° C.

$^1$H-NMR(CDCl$_3$,ppm): 0.87(3H,t.like),1.08(3H,s),1.14 (3H,s),1.2~1.5(10H,m),1.90(3H,brs),1.90(2H,m, overlapping), 2.42 (1H,d,J=13 Hz),2.48(1H,d,J=13 Hz),3.05 (1H,brm),3.22(1H,brm),3. 50(1H,t,J=10 Hz),4.14(1H,br), 4.61(1H,d,J=10 Hz),6.66(1H,brs),9.25(1H,br),9.45(1H,br)

EXAMPLE 12

5-hydroxy-4-(tert-butylamino)-2,6,6-trimethyl-2-cyclohepten-1-one

26% yield, colorless crystals, melting point: 103°~105° C.

$^1$H-NMR(CDCl$_3$,ppm): 0.99(3H,s),1.15(3H,s),1.84($^9$H,s) ,1.82(3H,t,J=2 Hz),2.34(1H,d,J=12 Hz),2.55(1H,d,J=12 Hz),2.82(1H,d,J=9 Hz),3.35(1H,m),6.36(1H,m)

Hydrochloride: 74% yield, colorless crystals

EXAMPLE 13

4-diethylamino-5-hydroxy-2,6,6-trimethyl-2-cyclohepten-1-one

48% yield, colorless plates, melting point: 71°~71.5° C.

$^1$H-NMR(CDCl$_3$,ppm): 0.98(3H,s),1.11(6H,t,J=7 Hz), 1.17(3H,s),1.84(3H,t,J=2 Hz),2.34(1H,d,J=12 Hz),2.48(1H, d,J=12 Hz),2.60(2H,br),3.12(1H,d,J=9 Hz),3.44(1H,dm,J=9 Hz),5.09(1H,s),6.43(1H,m)

Hydrochloride: 98% yield, colorless crystals, melting point: 186.5°~187.5° C. (decomposition)

EXAMPLE 14

4-di(1-propylamino)-5-hydroxy-2,6,6-trimethyl-2-cyclohepten-1-one hydrochloride

44% yield, colorless crystals, melting point: 180°~181.5° C. (decomposition)

$^1$H-NMR(CDCl$_3$,ppm): 1.02(3H,t,J=7 Hz),1.05(3H,t,J=7 Hz),1.14(3H,s),1.20(3H,s),1.95(3H,brs), 1.9~2.3(4H,m), 2.46(2H,s),2.8~3.0(1H,m),3.1~3.5(4H,m),4.30(1H,br.dd,J= 6,2 Hz),5.45(1H,br),6.42(1H,brs),10.7(1H,br)

EXAMPLE 15

5-hydroxy-4-pyrrolidino-2,6,6-trimethyl-2-cyclohepten-1-one hydrochloride

28% yield, colorless crystals $^1$H-NMR(CDCl$_3$,ppm): 1.13(3H,s),1.16(3H,s),1.95(3H,t, J=2 Hz),2.13~2.29(4H,m),2.46(1H,d,J=12 Hz),2.48(1H,d, J=12 Hz),3.04(1H,m),3.23(1H,m),3.37(1H,d,J=9 Hz),3.67 (2H,br),4.00(2H,m),4.38(1H,m),6. 28(1H,m),11.21(1H,brs)

EXAMPLE 16

5-hydroxy-4-piperidino-2,6,6-trinethyl-2-cyclohepten-1-one hydrochloride

52% yield, colorless crystals, melting point: 218.5°~219.5° C. (decomposition)

$^1$H-NMR(CD$_3$OD,ppm): 1.08(3H,s),1.09(3H,s),1.59~2.07(6H,m),1.93(3H,t,J=2 Hz),2.35(1H,d,J=12 Hz),2.66 (1H,d,J=12 Hz),3.19(1H,m),3.36(2H,m),3.42(1H,d,J=9 Hz), 3.58(1H,m),4.23(1H,m),6.84(1H,m)

The hydrochloride obtained here was dissolved in water, a 1N aqueous sodium hydroxide solution was added, and extraction with hexane and concentration yielded a free base. Colorless needles, melting point: 77.5°~79° C.

EXAMPLE 17

4-hexamethyleneimino-5-hydroxy-2,6,6-trimethyl-2-cyclohepten-1-one

71% yield, colorless needles, melting point: 82.5°~83.5° C.

$^1$H-NMR(CDCl$_3$,ppm): 0.98(3H,s),1.17(3H,s),1.5~1.9 (8H,br),1.85(3H,t,J=2 Hz),2.34(1H,d,J=12 Hz),2.46(1H,d, J=12 Hz),2.4~3.0(4H,br),3.14(1H,d,J=9 Hz),3.25(1H,m), 5.07(1H,s),6.39(1H,m)

Hydrochloride: 92.4% yield, colorless crystals, melting point: 209°~213° C. (decomposition)

EXAMPLE 18

5-hydroxy-4-morpholino-2,6,6-trimethyl-2-cyclohepten-1-one

66% yield, colorless crystals, melting point: 139°~140° C.

$^1$H-NMR(CDCl$_3$ppm): 0.99(3H,s),1.18(3H,s),1.88(3H,t, J=2 Hz),2.35(1H,d,J=12 Hz),2.48(1H,d,J=12 Hz),2.61(2H, m),2.75(2H,m),3.22(2H,m),3.76(4H,m),4.81(1H,s),6.43 (1H,m)

Hydrochloride: 87% yield, colorless powder, melting point: 213°~216° C. (decomposition)

EXAMPLE 19

4-(2-methylpiperidino)-5-hydroxy-2,6,6-trimethyl-2-cyclohepten-1-one hydrochloride 37% yield, colorless crystals, melting point: 183°~186° C. (decomposition)

EXAMPLE 20

4-(3-methylpiperidino)-5-hydroxy-2,6,6-trimethyl-2-cyclohepten-1-one hydrochloride 57% yield, colorless crystals, melting point: 197.5°~201° C. (decomposition)

EXAMPLE 21

4-(4-methylpiperidino)-5-hydroxy-2,6,6-trimethyl-2-cyclohepten-1-one hydrochloride 47% yield, colorless crystals, melting point: 232°~236° C. (decomposition)

EXAMPLE 22

5-hydroxy-4-(4-methylpiperazino)-2,6,6-trimethyl-2-cyclohepten-1-one

43% yield, colorless crystals

Hydrochloride: 98% yield, colorless powder, melting point: 229.5°~231.5° C. (foaming decomposition)

$^1$H-NMR(CD$_3$OD,ppm): 1.09(3H,s),1.10(3H,s),1.95(3H, t,J=2 Hz),2.37(1H,d,J=12 Hz),2.65(1H,d,J=12 Hz),3.02(3H, s),3.48(1H,d,J=9 Hz),3.56~3.85(8H,br),4.44(1H,m),6.82 (1H,m)

EXAMPLE 23

4-(4-hydroxypiperidino)-5-hydroxy-2,6,6-trimethyl-2-cyclohepten-1-one

57% yield, colorless oil $^1$H-NMR(CDCl$_3$,ppm): 0.98(3H,s),1.17(3H,s),1.50~1.78 (4H,m),1.86(3H,t,J=2 Hz),1.93~2.00(2H,m),2.29~2.49(3H, m),2.60~2.90(3H,m),2.23(2H,m),3.12(1H,brs),4.92(1H, brs), 6.41(1H,brs)

Hydrochloride: 74% yield, colorless crystals, melting point: 215.5°~222° C. (decomposition)

EXAMPLE 24

4-(4-ethoxycarbonylpiperidino)-5-hydroxy-2,6,6-trimethyl-2-cyclohepten-1-one

65% yield, colorless oil

Hydrochloride: 85% yield, colorless crystals, melting point: 120°~128° C. (decomposition)

$^1$H-NMR(CD$_3$OD,ppm):1.08(3H,s),1.10(3H,s),1.30(3H, t,J=7 Hz), 1.80~1.94(1H,m),2.36(1H,d,J=12 Hz),2.66(1H,d, J=12 Hz),3.25~3.50(4H,m),4.19(2H,q,J=7 Hz),4.31(1H,m), 6.84(1H,brs)

EXAMPLE 25

4-($^4$-carboxypiperidino)-5-hydroxy-2,6,6-trimethyl-2-cyclohepten-1-one

The 4-($^4$-ethoxycarbonylpiperidino)-5-hydroxy-2,6,6-trimethyl-2-cyclohepten-1-one obtained in Example 24 (0.68 g, 2.1 millimoles) was dissolved in acetic acid (5 ml), 6N hydrochloric acid (2 ml) was added and the mixture was heated at 80° C. for 90 minutes. Concentration to dryness followed by washing with ethyl acetate gave 0.56 g (80.2%) of 4-($^4$-carboxypiperidino)-5-hydroxy-2,6,6-trimethyl-2-cyclohepten-1-one hydrochloride.

Colorless crystals, melting point: 232°~233.5° C. (decomposition)

$^1$H-NMR(CD$_3$OD,ppm):1.08(3H,s),1.10($_3$H,s), 1.80~1.94(1H,m),1.94(3H,br),2.15~2.34(3H,m),2.36(1H,d, J=12 Hz),2.66(1H,d,J=12 Hz),2.75(1H,m),3.20~3.45(4H,m) ,3.67(1H,m),4.29(1H,m),6.83(1H,brs)

EXAMPLE 26

4-(1,4-dioxa-8-aza-spiro[5.4]decan-8-yl)-5-hydroxy-2,6, 6-trimethyl-2-cyclohepten-1-one 58% yield, colorless crystals, melting point: 167.5°~168.5° C.

$^1$H-NMR(CDCl$_3$,ppm): 0.98(3H,s),1.17(3H,s),1.58(1H,s) 1.79(4H,m),1.85(3H,n),2.33(1H,d,J=12 Hz), 2.47(1H,d,J= 12Hz),2.64(2H,m),2.81(2H,br),3.21(1H,d,J=9 Hz),3.26(1H, m),3.98(4H,s),4.91(1H,brs),6.44(1H,m)

Hydrochloride: 82% yield, colorless crystals, melting point: 220°~223° C. (decomposition)

EXAMPLE 27

4-(4-oxopiperidino)-5-hydroxy-2,6,6-trimethyl-2-cyclohepten-1-one

To an ethanol solution (5 ml) containing the 4-(1,4-dioxa-8-aza-spiro[4.5]decan-8-yl)-5-hydroxy-2,6,6-trimethyl-2-cyclohepten-1-one obtained in Example 26 (1 g, 3.24 millimoles) there was added 6N hydrochloric acid (2 ml), and the mixture was stirred at 75° C. for 4 hours. The reaction solution was concentrated, water was added, and a 1N aqueous sodium hydroxide solution was used for neutralization. The aqueous solution was subjected to extraction with ethyl acetate and drying over anhydrous magnesium sulfate. The crude product obtained by concentration of the ethyl acetate solution was recrystallized from a benzene-hexane mixed solvent to obtain 0.53 g (60.9%) of 4-(4-oxopiperidino)-5-hydroxy-2,6,6-trimethyl-2-cyclohepten-1-one as colorless crystals.

$^1$H-NMR(CDCl$_3$,ppm): 1.02(3H,s),1.20(3H,s),1.57(1H,s),1.86(3H,m),2.38(1H,d,J=12 Hz),2.42~2.60(5H,m),2.87 (2H,m),3.08(2H,m),2.28(1H,d,J=9 Hz),3.44(1H,m),4.63 (1H,s),6.32(1H,m)

This free base was treated with hydrogen chloride according to Example 1 to obtain 0.47 g (78%) of the hydrochloride as colorless crystals.

EXAMPLE 28

5-hydroxy-4-(N-methylbenzylamino)-2,6,6-trimethyl-2-cyclohepten-1-one

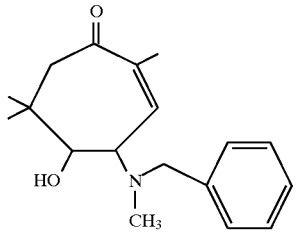

The 4-benzylamino-5-hydroxy-2,6,6-trimethyl-2-cyclohepten-1-one obtained in Example 1 (5.86 g, 21.5 millimoles) was dissolved in formic acid (30 ml), formalin (30 ml) was added, and the mixture was heated at 90° C. for 3 hours. The reaction solution was concentrated and alkalified with a 1% aqueous sodium hydroxide solution. The aqueous solution was subjected to extraction with benzene, washed with water, and then dried over anhydrous potassium carbonate. The benzene solution was concentrated, and the resulting residue was subjected to silica gel column chromatography with hexane-ethyl acetate (9:1) as the eluent, to obtain 2.95 g of crude product which was then recrystallized from hexane to give 2.39 g (39%) of 5-hydroxy-4-(N-methylbenzylamino)-2,6,6-trimethyl-2-cyclohepten-1-one as colorless crystals. Melting point: 78.5°~80° C.

$^1$H-NMR(CDCl$_3$,ppm): 0.81(3H,s),1.16(3H,s),1.89(3H,t, J=2 Hz),2.29(1H,d,J=12 Hz),2.33(3H,s),2.38(1H,d,J=12 Hz),3.23(1H,d,J=9 Hz),3.35(1H,m),3.65(1H,m),3.83(1H,d, J=13 Hz),4.94(1H,s),6.48(1H,m),7.25~7.39(5H,m)

EXAMPLE 29

5-hydroxy-4-piperidino-2,6,6-trimethyl-2-cyclohepten-1-one methyloxime

To a methanol solution (30 ml) containing the 5-hydroxy-4-piperidino-2,6,6-trimethyl-2-cyclohepten-1-one obtained in Example 16 (3 g, 12.5 millimoles) were added methoxyamine hydrochloride (1.57 g, 18.8 millimoles) and pyridine (3.0 g), and the mixture was stirred first at room temperature and then while slowly heating to 55° C., and after 5 hours of stirring at that temperature, it was allowed to stand at room temperature overnight. The reaction solution was then poured into water and alkalified with a 10% aqueous sodium hydroxide solution (20 ml). The aqueous solution was subjected to extraction with benzene and dried over anhydrous magnesium sulfate. The benzene solution was concentrated under reduced pressure, to obtain 3.49 g of 5-hydroxy-4-piperidino-2,6,6-trimethyl-2-cyclohepten-1-one methyloxime as crude crystals.

$^1$H-NMR(CDCl$_3$,ppm): 0.95(3H,s),1.32(3H,s), 1.20~1.65 (7H,br),1.81(1H,d,J=12 Hz),1.93(3H,m),2,45(2H,br),2.64 (2H,m),1.92(1H,d,J=12 Hz),3.08(1H,m),3.19(1H,d,J=9 Hz), 3.83(3H,s),5.14(1H,brs),5.84(1H,brs)

The obtained crude crystals of the free base were treated with hydrogen chloride according to Example 1 to obtain 3.65 g (93%) of the hydrochloride. Melting point: 250°~257° C.

Compounds of Examples 30 and 31 were obtained in the same manner as Example 29. The compound of Example 30 was also acetylated to obtain the compound of Example 32.

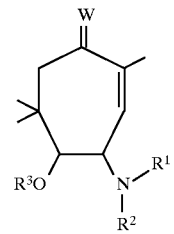

| Example | R$^1$ | R$^2$ | R$^3$ | W |
|---|---|---|---|---|
| 29 | —(CH$_2$)$_5$— | | H | NOCH$_3$ |
| 30 | —(CH$_2$)$_5$— | | H | NOH |
| 31 | —(CH$_2$)$_4$— | | H | NOH |
| 32 | —(CH$_2$)$_5$— | | AC | NOAC |

EXAMPLE 30

5-hydroxy-4-piperidino-2,6,6-trimethyl-2-cyclohepten-1-one oxime

Hydrochloride: 96% yield, colorless powder, melting point 237°~242° C. (decomposition)

Free base: colorless crystals $^1$H-NMR(CDCl$_3$,ppm): 0.98(3H,s),1.18(3H,s),1.20~1.70 (7H,br),183(1H,d,J=13 Hz),1.92(3H,m),2.46(2H,br),2.66 (2H,m),2.03(1H,d,J=13 Hz),3.10(1H,m),3.20(1H,d,J=9 Hz), 5.15(1H,brs),5.88(1H,brs),8.03(1H,brs)

EXAMPLE 31

5-hydroxy-4-pyrrolidino-2,6,6-trimethyl-2-cyclohepten-1-one oxime

Hydrochloride: 84% yield, colorless crystals, melting point: 241°~242° C. (decomposition)

$^1$H-NMR(CD$_3$OD,ppm): 1.03(3H,s),1.07(3H,s),1.79(1H, d,J=13 Hz),1.99(3H,br),2.0~2.2(4H,m),3.18(1H,d,J=13 Hz),3.15~3.23(1H,m),3.35(1H,d,J=10 Hz),3.36~3.45(2H, m),3.53~3.62(1H,m),3.31(1H,brd,J=10 Hz),5.77(1H,br)

EXAMPLE 32

5-acetoxy-4-piperidino-2,6,6-trimethyl-2-cyclohepten-1-one acetoxime

Hydrochloride: 93% yield, colorless crystals

Free base: colorless oil $^1$H-NMR(CDCl$_3$,ppm): 1.02(6H,s),1.15~1.62(6H,br), 2.03(3H,m),2.10(3H,s),2.22(3H,s),2.39(1H,d,J=14 Hz),2.44 (2H,m),2.58(2H,m),2.77(1H,d,J=12 Hz),3.31(1H,m),4.83 (1H,d,J=9 Hz),5.01(1H,brs)

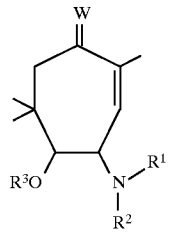

| Example | Step | R$^1$ | R$^2$ | R$^3$ | W |
|---|---|---|---|---|---|
| 33 | 1 | —CH$_2$—Ph | A$_C$ | H | O |
|  | 2 | —CH$_2$—Ph | A$_C$ | H | NOCH$_3$ |
|  | 3 | —CH$_2$—Ph | A$_C$ | CH$_3$ | NOCH$_3$ |
|  | 4 | —CH$_2$—Ph | H | CH$_3$ | O |
| 34 | 1 | Ph | H | A$_C$ | O |
|  | 2 | Ph | H | A$_C$ | NOCH$_3$ |
|  | 3 | Ph | A$_C$ | CH$_3$ | NOCH$_3$ |
|  | 4 | Ph | H | CH$_3$ | O |

EXAMPLE 33

4-benzylamino-5-methoxy-2,6,6-trimethyl-2-cyclohepten-1-one

Step 1

The 4-benzylamino-5-hydroxy-2,6,6-trimethyl-2-cyclohepten-1-one obtained in Example 1 (17.3 g, 63.4 millimoles) was dissolved in tetrahydrofuran (100 ml), triethylamine (19.2 g, 190 millimoles) was added, and acetic anhydride (12.9 g, 127 millimoles) was added dropwise while stirring on ice. After heating the reaction solution at 50° C. for 3 hours, it was poured into ice water (300 ml). After 30 minutes the aqueous solution was subjected to extraction with benzene, washed with water, and then dried over anhydrous magnesium sulfate. The benzene was distilled off, and the resulting residue was recrystallized from a mixed solvent of ethyl acetate and hexane to obtain 19.0 g (95%) of 4-(N-acetylbenzylamino)-5-hydroxy-2,6,6-trimethyl-2-cyclohepten-1-one.

Step 2

The 4-(N-acetylbenzylamino)-5-hydroxy-2,6,6-trimethyl-2-cyclohepten-1-one obtained in step 1 (19.0 g, 60.3 millimoles) was treated according to Example 29, to obtain 14.5 g (70%) of 4-(N-acetylbenzylamino)-5-hydroxy-2,6,6-trimethyl-2-cyclohepten-1-one methyloxime as a colorless oil.

Step 3

To a solution of tetrahydrofuran (40 ml) containing the 4-(N-acetylbenzylamino)-5-hydroxy-2,6,6-trimethyl-2-cyclohepten-1-one methyloxime obtained in step 2 (9.5 g, 27.6 millimoles) there was gradually added 55% sodium hydride (3.6 g) while cooling on ice. After then adding methyl iodide (7.8 g, 55.2 millimoles) and stirring for 30 minutes, the mixture was returned to room temperature and stirring was continued for one hour. The reaction solution was poured into ice water (100 ml) containing acetic acid (1 ml), and subjected to extraction with benzene. After washing the benzene solution with water, it was dried over anhydrous magnesium sulfate. The benzene was distilled off, and the resulting residue was subjected to silica gel column chromatography with benzene-ethyl acetate (9:1) as the eluent, to obtain 8.51 g (86%) of 4-(N-acetylbenzylamino)-5-methoxy-2,6,6-trimethyl-2-cyclohepten-1-one methyloxime as a colorless oil.

Step 4

To a solution of ethanol (40 ml) containing the 4-(N-acetylbenzylamino)-5-methoxy-2,6,6-trimethyl-2-cyclohepten-1-one methyloxime obtained in step 3 (8.5 g, 23.7 millimoles) there were added pyruvic acid (4.18 g, 47.4 millimoles) and 6N hydrochloric acid (40 ml), and the mixture was heated at 75° C. for 4 hours. The reaction solution was concentrated and the resulting residue was dissolved in methanol (50 ml) and then neutralized with a 10% aqueous sodium hydroxide solution while stirring on ice. Water (100 ml) was added, extraction was performed with benzene, and after washing the benzene solution with water it was dried over anhydrous magnesium sulfate. The benzene was distilled off and the resulting residue was subjected to silica gel column chromatography with benzene-ethyl acetate (19:1) as the eluent, to obtain 4.72 g (69%) of 4-benzylamino-5-methoxy-2,6,6-trimethyl-2-cyclohepten-1-one as a colorless oil.

$^1$H-NMR(CDCl$_3$,ppm): 0.90(3H,s),1.12(3H,s),1.84(3H,t, J=2 Hz),2.25(1H,d,J=12 Hz),2.51(1H,d,J=12 Hz),2.83(1H, d,J=9 Hz)3.52 (3H,s),3.50~3.56(1H,m),3.78(1H,d,J=14 Hz),4.05(1H,d,J=14 Hz),6.61(1H,m),7.30(5H,m)

EXAMPLE 34

5-methoxy-4-phenylamino-2,6,6-trimethyl-2-cyclohepten-1-one

Step 1

The 5-hydroxy-4-phenylamino-2,6,6-trimethyl-2-cyclohepten-1-one obtained in Example 5 (13.7 g) was treated according to step 1 of Example 33 and crystallized from a mixed solvent of benzene and hexane, to obtain 14.6 g (92%) of 5-acetoxy-4-phenylamino-2,6,6-trimethyl-2-cyclohepten-1-one as colorless crystals.

$^1$H-NMR(CDCl$_3$,ppm): 1.03(3H,s),1.15(3H,s),1.78(3H,s) ,1.86(3H,t,J=2 Hz),2.47(1H,d,J=12 Hz),2.72(1H,d,J=12 Hz),3.7~ 4.1(1H,brs),4.45(1H,m),4.73(1H,d,J=9 Hz),6.42 (1H,m),6.61(2H,m),6.74(1H,m),7.18(2H,m)

Step 2

5-acetoxy-4-phenylamino-2,6,6-trimethyl-2-cyclohepten-1-one methyloxime

The 5-acetoxy-4-phenylamino-2,6,6-trimethyl-2-cyclohepten-1-one obtained in step 1 (4.0 g) was treated according to Example 29 to obtain 3.27 g (75%) of 5-acetoxy-4-phenylamino-2,6,6-trimethyl-2-cyclohepten-1-one methyloxime as colorless crystals.

$^1$H-NMR(CDCl$_3$,ppm): 0.97(3H,s),1.14(3H,s),1.72(3H, s), 1.92(3H,t,J=2 Hz),2.04(1H,d,J=13 Hz),3.08(1H,d,J=13 Hz),3.7~4.0(1H,brs),3.90(3H,s),4.36(1H,m),4.69(1H,d,J=9 Hz),5.77(1H,m),6.58(2H,m),6.69(1H,m),7.15(2H,m)

Step 3

5-methoxy-4-(N-acetylphenylamino)-2,6,6-trimethyl-2-cyclohepten-1-one methyloxime The 5-acetoxy-4-phenylamino-2,6,6-trimethyl-2-cyclohepten-1-one methyloxime obtained in step 2 (3.27 g) was treated according to step 3 of Example 33 to obtain 2.11 g (62%) of 5-methoxy-4-(N-acetylphenylamino)-2,6,6-trimethyl-2-cyclohepten-1-one methyloxime as a colorless oil.

$^1$H-NMR(CDCl$_3$,ppm): 0.88(3H,s),1.11(3H,s),1.80(1H,d, J=13 Hz),1.85(3H,s),1.92(3H,t,J=2 Hz),2.82(1H,d,J=13 Hz),3.51(3H,s),3.64(1H,d,J=9 Hz),3.86(3H,s),4.04(1H,m), 6.07(1H,d),7.30(5H,m)

Step 4

5-methoxy-4-phenylamino-2,6,6-trinethyl-2-cyclohepten-1-one

The 5-methoxy-4-(N-acetylphenylamino)-2,6,6-trimethyl-2-cyclohepten-1-one methyloxime obtained in step 3 (1.66 g) was treated according to step 4 of Example 33 to obtain 0.68 g (52%) of 5-methoxy-4-phenylamino-2,6,6-trimethyl-2-cyclohepten-1-one as a colorless oil.

$^1$H-NMR(CDCl$_3$,ppm): 1.01(3H,s),1.15(3H,s),1.84(3H,t,J=2 Hz),2.38(1H,d,J=12 Hz),2.71 (1H,d,J=12 Hz),3.02(1H,d,J=9 Hz),3.60(3H,s),4.07(1H,m),6.56(1H,m),6.73(2H,m),6.84(1H,m),7.25(2H,m)

EXAMPLE 35

(+) and (−)-5-hydroxy-4-piperidino-2,6,6-trimethyl-2-cyclohepten-1-one

To an ethanol solution (20 ml) containing the 5-hydroxy-4-piperidino-2,6,6-trimethyl-2-cyclohepten-1-one obtained in Example 16 (5.0 g, 20 millimoles) was added an ethanol solution (20 ml) containing (−)-dibenzoyl tartrate (3.76 g, 10 millimoles), and the resulting crystals were filtered and dissolved in methanol (30 ml). After concentrating the solution it was recrystallized from ethanol to obtain 3.3 g of dibenzoyl tartrate salt. This was dissolved in water, alkalified with a 10% aqueous sodium hydroxide solution, and the aqueous solution was subjected to extraction with hexane. The residue obtained from concentrating the hexane solution was recrystallized from hexane to obtain 1.6 g (32%) of (+)-5-hydroxy-4-piperidino-2,6,6-trimethyl-2-cyclohepten-1-one as colorless needles. [α]D$^{20}$: +119° (c=1.00, ethanol).

Melting point: 69°~70° C. Hydrochloride: colorless crystals, melting point: 227°~228° C. (decomposition).

The first crystalline mother liquid was concentrated, alkalified with a 10% aqueous sodium hydroxide solution and extraction was performed with hexane. The residue obtained by concentrating the hexane solution was dissolved in ethanol (20 ml), and an ethanol solution (20 ml) containing (+)-dibenzoyl tartrate (3.15 g, 8.4 millimoles) was added thereto. The procedure described above was then followed to obtain 1.5 g (30%) of (−)-5-hydroxy-4-piperidino-2,6,6-trimethyl-2-cyclohepten-1-one. [α]D$^{20}$: −119° (c=1.00, ethanol). Melting point: 71°~ 2° C. Hydrochloride: colorless crystals, melting point: 226°~228° C. (decomposition).

We claim:

1. A 4-amino-5-oxy-2,6,6-trimethyl-2-cycloheptene compound represented by the general formula:

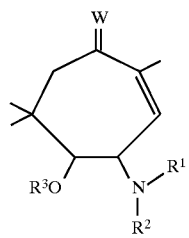

(wherein R$^1$ and R$^2$ each independently represent a hydrogen atom, an alkyl group of 1 to 10 carbon atoms which may have a substituent, or a phenyl group which may have a hydroxyl group, lower alkoxy group, amino group, nitro group, carboxyl group, lower alkoxycarbonyl group or halogen atom, or R$^1$, R$^2$ and the nitrogen atom together represent a saturated nitrogen heterocyclic group; R$^3$ represents a hydrogen atom, a lower alkyl group or a lower aliphatic acyl group; and W represents an oxo group, oxime group or oxime ether group); or a pharmacologically acceptable salt or a solvate thereof.

2. A compound according to claim 1, wherein the alkyl group of R$^1$ and/or R$^2$ is an alkyl group of 1 to 10 carbon atoms substituted with a lower alkoxy group, amino group, lower alkylamino group, lower dialkylamino group or a phenyl group which may have a hydroxyl group, lower alkoxy group, amino group, nitro group, carboxyl group, lower alkoxycarbonyl group or halogen atom on the ring; or a pharmacologically acceptable salt or a solvate thereof.

3. A compound according to claim 1, wherein the saturated nitrogen heterocyclic group is pyrrolidine, piperidine, homopiperidine, piperazine, homopiperazine or morpholine which may have a lower alkyl group, hydroxyl group, lower alkoxy group, carboxyl group, lower alkoxycarbonyl group, oxo group or an acetal group thereof on its ring, or a pharmacologically acceptable salt or a solvate thereof.

4. A compound according to claim 1 which is 5-hydroxy-4-piperidino-2,6,6-trimethyl-2-cyclohepten-1-one, or a pharmacologically acceptable salt or a solvate thereof.

5. A pharmaceutical composition whose effective component is a 4-amino-5-oxy-2,6,6-trimethyl-2-cycloheptene compound represented by the general formula:

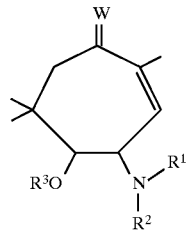

(wherein R$^1$ and R$^2$ each independently represent a hydrogen atom, an alkyl group of 1 to 10 carbon atoms which may have a substituent, or a phenyl group which may have a hydroxyl group, lower alkoxy group, amino group, nitro group, carboxyl group, lower alkoxycarbonyl group or halogen atom, or R$^1$, R$^2$ and the nitrogen atom together represent a saturated nitrogen heterocyclic group; R$^3$ represents a hydrogen atom, a lower alkyl group or a lower aliphatic acyl group; and W represents an oxo group, oxime group or oxime ether group); or a pharmacologically acceptable salt or a solvate thereof.

6. A method of using the pharmaceutical composition of claim 5 for treating hypertension, peripheral arterial occlusion, or bronchial asthma in a subject, the method comprising: administering to the subject an effective amount of the pharmaceutical composition for correspondingly treating hypertension, peripheral aterial occlusion, or bronchial asthma.

7. A compound according to claim 3 which is 5-hydroxy-4-piperidino-2,6,6-trimethyl-2-cyclohepten-1-one, or a pharmacologically acceptable salt or a solvate thereof.

* * * * *